(12) United States Patent
Murthy et al.

(10) Patent No.: US 7,141,641 B2
(45) Date of Patent: Nov. 28, 2006

(54) METHOD AND APPARATUS FOR PRODUCTION OF ALKYL ARYL ETHER AND DIARYL CARBONATE

(75) Inventors: Vutukuru Lakshmi Narasimha Murthy, Bangalore (IN); Ignacio Fernandez Vic, Las Matas (ES); Ganesh Kailasam, Evansville, IN (US); Alberto Nisoli, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 18 days.

(21) Appl. No.: 10/604,099

(22) Filed: Jun. 26, 2003

(65) Prior Publication Data

US 2004/0266974 A1    Dec. 30, 2004

(51) Int. Cl.
*C08G 64/00* (2006.01)
(52) U.S. Cl. .................. 528/196; 203/57; 203/60; 203/63; 203/64; 203/65; 422/131; 528/198; 558/268; 558/274
(58) Field of Classification Search .............. 203/57, 203/60, 63, 64, 65; 422/131; 528/196, 198; 558/268, 274
See application file for complete search history.

(56) References Cited

U.S. PATENT DOCUMENTS

| | | | |
|---|---|---|---|
| 4,182,726 A | 1/1980 | Illuminati et al. | |
| 4,410,464 A | 10/1983 | Hallgren et al. | |
| 5,166,393 A | 11/1992 | Fukuoka et al. | |
| 5,210,268 A | 5/1993 | Fukuoka et al. | |
| 5,426,207 A * | 6/1995 | Harrison et al. | 558/274 |
| 5,705,673 A | 1/1998 | Rivetti et al. | |
| 5,760,156 A | 6/1998 | Inoki et al. | |
| 5,872,275 A | 2/1999 | Komiya et al. | |
| 6,168,382 B1 | 1/2001 | Nolan et al. | |
| 6,294,682 B1 | 9/2001 | Rauleder et al. | |
| 6,294,684 B1 | 9/2001 | de Bruin et al. | |
| 6,294,685 B1 | 9/2001 | Ushikubo et al. | |
| 6,315,868 B1 * | 11/2001 | Nisoli et al. | 203/57 |
| 2001/0021786 A1 * | 9/2001 | Bruin et al. | 558/268 |

FOREIGN PATENT DOCUMENTS

| | | |
|---|---|---|
| EP | 0 461 274 | 6/1994 |
| EP | 0781 760 B1 | 9/2002 |
| WO | WO 92/18458 | 10/1992 |
| WO | WO 01/42187 A1 | 6/2001 |

OTHER PUBLICATIONS

JP1997059225A. Publication Date Mar. 4, 1997. (Machine Translation).
International Search Report Mailed on Jan. 3, 2005.

* cited by examiner

*Primary Examiner*—Terressa Boykin

(57) ABSTRACT

A method and apparatus for continuously producing an alkyl aryl ether and a diaryl carbonate by reacting a dialkyl carbonate and an aromatic alcohol in presence of a transesterification catalyst.

25 Claims, 3 Drawing Sheets

METHOD AND APPARATUS FOR PRODUCTION OF ALKYL ARYL ETHER AND DIARYL CARBONATE

BACKGROUND

This disclosure relates to an energy efficient method and apparatus for production of an alkyl aryl ether and a diaryl carbonate.

Diaryl carbonates, such as diphenyl carbonate are an important reactant in the production of polycarbonate resins. As the use of polycarbonate resins has increased, the efficient production of diaryl carbonate has become of greater importance because polycarbonates can be manufactured by reacting bisphenols (e.g., Bisphenol A) with diaryl carbonates. Diaryl carbonate production involves two reaction steps. First, a dialkyl carbonate reacts with an aromatic alcohol to produce an alkyl aryl carbonate and an alkyl alcohol in presence of a transesterification catalyst. Next, two molecules of the alkyl aryl carbonate undergo a disproportionation reaction to produce one molecule of diaryl carbonate and one molecule of dialkyl carbonate. Alkyl aryl ether, such as anisole, is a side product in this process and is produced by the reaction of dialkyl carbonate and aromatic alcohol. Alkyl aryl ether is also produced by decarboxylation reaction of alkyl aryl carbonate.

The side product alkyl aryl ether from diaryl carbonate production is purged from the process along with aromatic alcohol and dialkyl carbonate. This purged stream comprising alkyl aryl ether may not be suitable for use in any other synthesis as it may contain dialkyl carbonate and aromatic alcohol. So while there is a process to purge alkyl aryl ether from diaryl carbonate manufacturing process, currently there is no process for co-production of alkyl aryl ether along with diaryl carbonate in an energy efficient process.

SUMMARY

Disclosed herein is a method and apparatus for continuously producing an alkyl aryl ether. The method comprises reacting a dialkyl carbonate and an aromatic alcohol in the presence of a transesterification catalyst in a first reactive distillation column, recovering from the first reactive distillation column a stream comprising dialkyl carbonate, alkyl alcohol and alkyl aryl ether, separating the dialkyl carbonate and alkyl alcohol from alkyl aryl ether in a rectification column and recovering from the rectification column a first product stream comprising substantially pure alkyl aryl ether.

In another embodiment a method and apparatus for continuously producing a diaryl carbonate and an alkyl aryl ether comprises reacting a dialkyl carbonate and an aromatic alcohol in the presence of a transesterification catalyst in a first reactive distillation column. Two streams are recovered from first reactive distillation column, a first top stream and a first bottom stream. The first top stream comprising dialkyl carbonate, alkyl alcohol and alkyl aryl ether is split into two streams, a first split stream and a second split stream. The first split stream is introduced to a first rectification column and the second split stream is introduced to a second rectification column. Two streams are recovered from the first rectification column, a second top stream and a third bottom stream. The second top stream comprises dialkyl carbonate and alkyl alcohol. Part or all of the third bottom stream comprising dialkyl carbonate and alkyl aryl ether is recycled to the first reactive distillation column. A first product stream is recovered from the bottom of the second rectification column comprising substantially pure alkyl aryl ether. A recycle stream comprising dialkyl carbonate and alkyl alcohol is recovered from the top of the second rectification column and is recycled to the first reactive distillation column.

The first bottom stream comprising alky aryl carbonate, dialkyl carbonate, diaryl carbonate, aromatic alcohol and transesterification catalyst is introduced to a second reactive distillation column. A second bottom stream comprising diaryl carbonate, alkyl aryl carbonate, dialkyl carbonate, aromatic alcohol and alkyl aryl ether is recovered from the second reactive distillation column and is introduced to a third reactive distillation column. A second product stream comprising diaryl carbonate produced is recovered from the bottom of the third reactive distillation column. A third top stream comprising aromatic alcohol, dialkyl carbonate and alkyl aryl ether is recovered from the top of the third reactive distillation column and is recycled to the first reactive distillation column.

DETAILED DESCRIPTION

Figure 1:
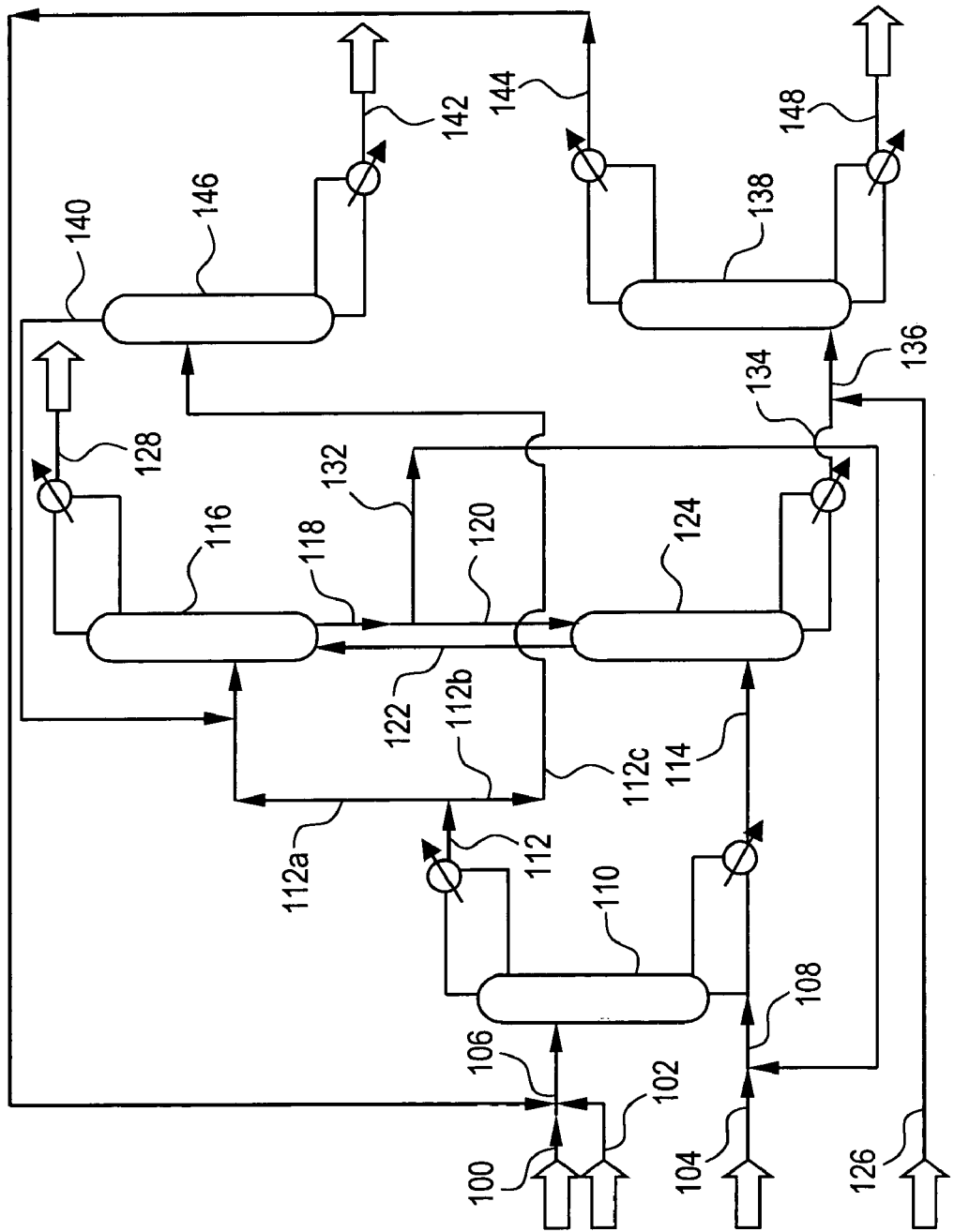
FIG. 1 shows a schematic representation of an exemplary process for producing alkyl aryl ether and diaryl carbonate.

Disclosed herein is a method and apparatus for continuously producing an alkyl aryl ether. The method comprises reacting a dialkyl carbonate and an aromatic alcohol in the presence of a transesterification catalyst in a first reactive distillation column, recovering from the first reactive distillation column a stream comprising dialkyl carbonate, alkyl alcohol and alkyl aryl ether, separating the dialkyl carbonate and alkyl alcohol from alkyl aryl ether in a rectification column and recovering from the rectification column a first product stream comprising substantially pure alkyl aryl ether. Substantially pure is defined herein as having a purity of at least about 95% by weight, preferably at least about 99% by weight and up to about 100% by weight and all subranges therebetween.

In another embodiment a method and apparatus for continuously producing a diaryl carbonate and an alkyl aryl ether comprises reacting a dialkyl carbonate and an aromatic alcohol in the presence of a transesterification catalyst in a first reactive distillation column. Two streams are recovered from first reactive distillation column, a first top stream and a first bottom stream. The first top stream comprising dialkyl carbonate, alkyl alcohol and alkyl aryl ether is split into two streams, a first split stream and a second split stream. The first split stream is introduced to a first rectification column and the second split stream is introduced to a second rectification column. Two streams are recovered from the first rectification column, a second top stream and a third bottom stream. The second top stream comprises dialkyl carbonate and alkyl alcohol. Part or all of the third bottom stream comprising dialkyl carbonate and alkyl aryl ether is recycled to the first reactive distillation column. A first product stream is recovered from bottom of the second rectification column comprising substantially pure alkyl aryl ether. A recycle stream comprising dialkyl carbonate and alkyl alcohol is recovered from the top of the second rectification column and is recycled to the first reactive distillation column.

Purging of alkyl aryl ether rich stream from the first reactive distillation column facilitates purification of the alkyl aryl ether. It also helps in reducing the utility consumption of the process disclosed herein as a reduced amount of alkyl aryl ether is present in the streams entering the reboilers and condensers of the reactive distillation columns. High recirculation rate of alkyl aryl ether occupies volume in the reactive distillation columns, which reduces the volume available for diaryl carbonate formation reactions. Purging alkyl aryl ether from the first reactive distillation column facilitates an increase in the available volume in the downstream reactive distillation columns for the formation of diaryl carbonate.

The first bottom stream comprising alky aryl carbonate, dialkyl carbonate, diaryl carbonate, aromatic alcohol and transesterification catalyst is introduced to a second reactive distillation column. A second bottom stream comprising diaryl carbonate, alkyl aryl carbonate, dialkyl carbonate, aromatic alcohol and alkyl aryl ether is recovered from the second reactive distillation column and is introduced to a third reactive distillation column. A second product stream comprising diaryl carbonate produced is recovered from the bottom of the third reactive distillation column. A third top stream comprising aromatic alcohol, dialkyl carbonate and alkyl aryl ether is recovered from the top of the third reactive distillation column and is recycled to the first reactive distillation column.

The disclosed method comprises an energy efficient series of mass and energy integrated processes to affect the co production of diaryl carbonate and alkyl aryl ether.

The principal reactions are illustrated as follows. Diaryl carbonate production involves two reaction steps. First a dialkyl carbonate reacts with an aromatic alcohol to produce an alkyl aryl carbonate and an alkyl alcohol in presence of a transesterification catalyst. Next two molecules of alkyl aryl carbonate undergo a disproportionation reaction to produce one molecule of diaryl carbonate and one molecule of dialkyl carbonate. Reaction (1) has low reaction equilibrium constant and conversion of the limiting reactant is not complete resulting in large recycles of dialkyl carbonate and aromatic alcohol.

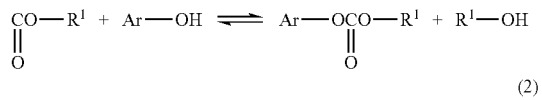

(1)

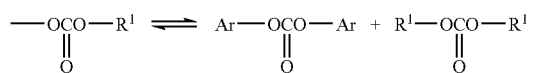

(2)

Dialkyl carbonates may be described by general formula (I) herein below

(I)

wherein $R^1$ is an alkyl group having one to about 30 carbon atoms and each occurrence of $R^1$ is independently an alkyl group. More explicitly the alkyl group may be same or different at each occurrence.

Specific examples of $R^1$ include alkyl groups such as methyl groups, ethyl groups, propyl groups, butyl groups, pentyl groups, hexyl groups, heptyl groups, octyl groups, nonyl groups, and decyl groups. Suitable dialkyl carbonates, which are useful in the present reactions, include dimethylcarbonate, diethylcarbonate, methylethylcarbonate, ethylpropylcarbonate, dipropylcarbonate, propylbutylcarbonate, dibutylcarbonate, butylpentylcarbonate, dipentylcarbonate, pentylhexylcarbonate, dihexylcarbonate, hexylheptylcarbonate, diheptylcarbonate, heptyloctylcarbonate, dioctylcarbonate, octyinonylcarbonate, dinonylcarbonate, nonyldecylcarbonate, and didecylcarbonate. The preferred dialkyl carbonate is dimethyl carbonate.

The aromatic alcohol compound used to manufacture aromatic carbonates is described by general formula (II):

I  (II)

wherein Ar is a monovalent aromatic group, which may have a substituent.

Examples of such aromatic alcohols include phenol and alkylphenols such as cresol, xylenol, trimethylphenol, tetramethylphenol, ethylphenol, propylphenol, butylphenol, diethylphenol, methylethylphenol, methylpropylphenol, dipropylphenol, methylbutylphenol, pentylphenol, hexylphenol, and cyclohexylphenol. The preferred aromatic alcohol is phenol.

Specific examples of alkyl aryl carbonates that can be obtained by means of reaction (1) include methyl phenyl carbonate, ethyl phenyl carbonate, propyl phenyl carbonate, allyl phenyl carbonate, butyl phenyl carbonate, pentyl phenyl carbonate, hexyl phenyl carbonate, heptyl phenyl carbonate, octyl tolyl carbonate, nonyl (ethylphenyl) carbonate, decyl (butylphenyl) carbonate, methyl tolyl carbonate, ethyl tolyl carbonate, propyl tolyl carbonate, butyl tolyl carbonate, allyl tolyl carbonate, ethyl xylyl carbonate, methyl (trimethylphenyl) carbonate, methyl (chlorophenyl) carbonate, methyl (nitrophenyl) carbonate, methyl (methoxyphenyl) carbonate, methyl cumyl carbonate, methyl (naphthyl) carbonate, methyl (pyridyl) carbonate, ethyl cumyl carbonate, methyl (benzoylphenyl) carbonate, ethyl xylyl carbonate, benzyl xylyl carbonate, methyl (hydroxyphenyl) carbonate, ethyl (hydroxyphenyl) carbonate, methoxycarbonyloxybiphenyl, methyl (hydroxybiphenyl) carbonate, methyl 2-(hydroxyphenyl)propylphenyl carbonate, and ethyl 2-(hydroxyphenyl)propylphenyl carbonate.

Preferred classes of transesterification catalysts include titanium compounds like titaniumtetraphenoxide $(Ti(OPh)_4)$, and titaniumtetrachloride, organotin compounds, and compounds of copper, lead, zinc, iron, and zirconium.

Side reactions occur in the process of producing diaryl carbonate, such as reaction (3), which shows the formation of an alkyl aryl ether where dialkyl carbonate reacts with aromatic alcohol. Reaction (4) shows another route for production of alkyl aryl ether, wherein alkyl aryl carbonate decarboxylizes to produce alkyl aryl ether. Alkyl aryl ether produced by these reactions is purged from the diaryl carbonate production process for steady operation of the production process and to avoid unwanted build up in recirculation streams. The alkyl aryl ether such as anisole is a by-product of the reaction of dialkyl carbonate and aromatic alcohol as shown in reaction (3). Anisole is usually the by-product of the reaction of dimethyl carbonate and phenol.

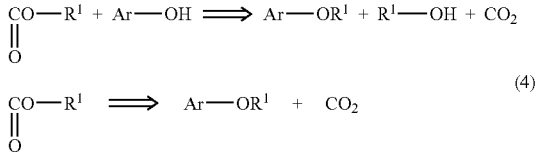

Figure 2:
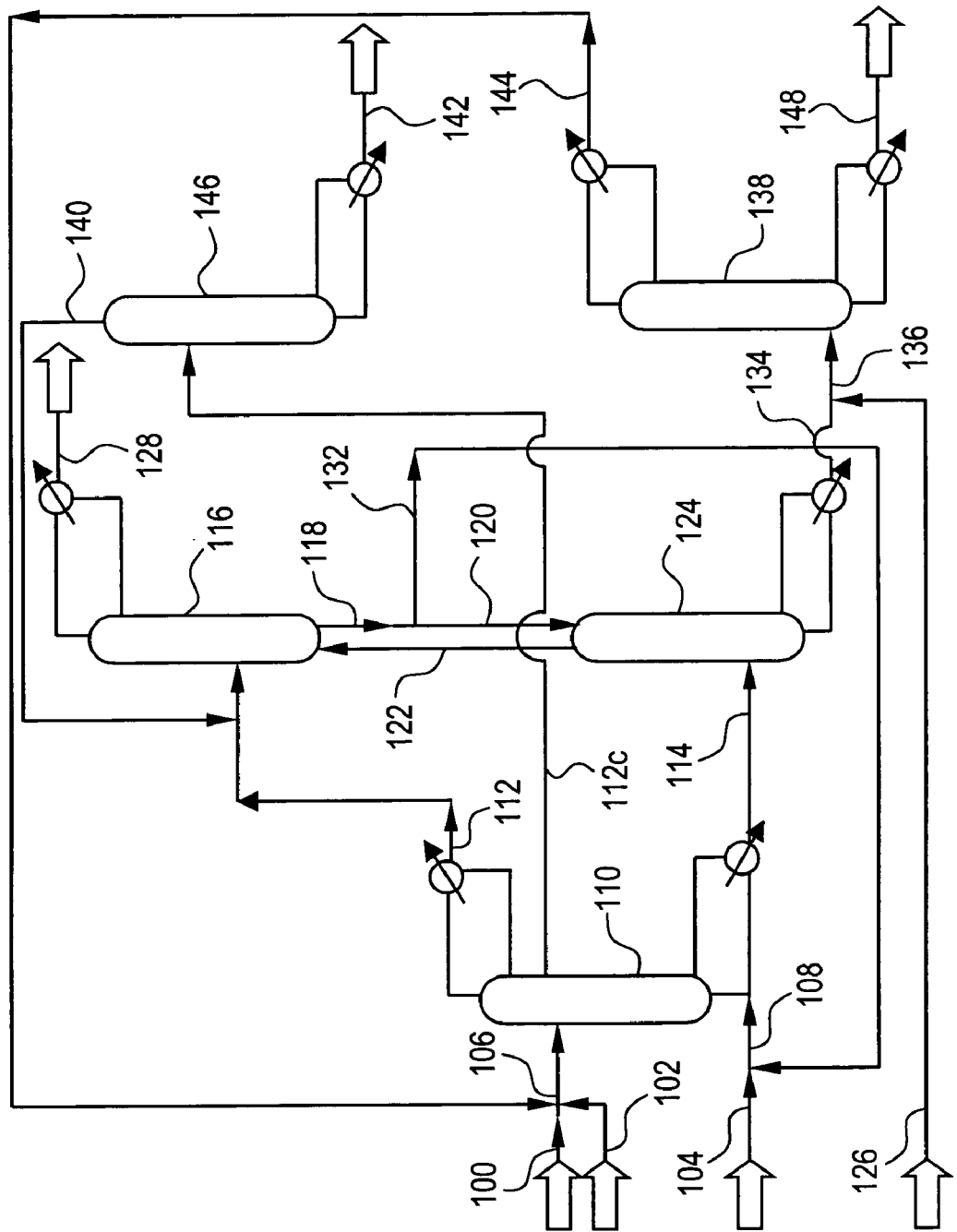
FIG. 2 shows another schematic representation of an exemplary process for producing alkyl aryl ether and diaryl carbonate.

FIG. 1 and FIG. 2. show schematic representations of exemplary apparatus for co-production of diaryl carbonate and alkyl aryl ether. In the figures, which are exemplary embodiments, the like elements are numbered alike. The apparatus comprises five columns 110, 124, 138, 116 and 146 and various feed, product and recycle streams as indicated by the numbers 100–148. The direction of flow for each stream is indicated in FIG. 1 and FIG. 2. Various valves, heaters, and other fittings may be included in adapting the design to a particular installation, and the inclusion of such components is within the skill in the art.

Columns 110, 124 and 138 are reactive distillation columns. While reactive distillation columns are preferred, the reaction forming alkyl aryl ether may be accomplished in any batch or continuous reactor. Reactive distillation columns each have a lower reaction section in which a chemical reaction occurs and an upper rectification section. The construction of columns of this type is known in the art. In general, the reactive and rectification sections of the column will be furnished with arranged packings, dumped packings or fixed internals. Column 110 provides about 10 to about 80, and more preferably about 15 to about 60 theoretical distillation stages, and all subranges therebetween.

The side reaction forming alkyl aryl ether takes place in all reactive distillation columns, although the maximum amount of alkyl aryl ether is produced in the first reactive distillation column where alkyl aryl carbonate is formed. In one embodiment as shown in FIG. 1, the top stream 112 drawn from the first reactive distillation column, 110 is split into two streams 112a and 112b. Stream 112b is sent to second rectification column 146 for purification of alkyl aryl ether. Another embodiment as shown in FIG. 2, a side stream 112c is drawn from the first reactive distillation column 110. Stream 112c is sent to second rectification column 146 for purification of alkyl aryl ether. Streams 112b and 112c may comprise up to about 25% alkyl aryl ether by weight along with alkyl alcohol and dialkyl carbonate.

The decarboxylation reaction (4) is favored in the presence of aromatic alcohol. Alkyl aryl ether may be formed in any stream rich in alkyl aryl carbonate through the decarboxylation route at a suitable reaction condition.

In one embodiment, as shown in FIG. 2 the alkyl aryl ether rich stream 112c from the first reactive distillation column may be drawn at a location that is above the location of the feed into the column. In a preferred embodiment the location of the feed stream 106 is above the reactive section of the reactive distillation column 110. Column 110 is operated under conditions such that the concentration of aromatic alcohol is reduced in the alkyl aryl ether rich side stream since presence of aromatic alcohol may affect the purification of alkyl aryl ether in second rectification column 146. In order to reduce the concentration of aromatic alcohol in the side stream 112c, the reactive distillation column is operated at high reflux flow. The concentration of aromatic alcohol decreases along the height of the column and the concentration will be negligible at the top of the column. However the concentration of alkyl aryl ether also decreases along with the height of the column. So an optimum position is chosen for drawing of the alkyl aryl ether rich stream where the concentration of alkyl aryl ether is high and concentration of aromatic alcohol is not high enough to affect the purification of alkyl aryl ether.

Columns 116 and 146 are rectification columns. These columns are intended to carry out a separation of materials based upon boiling point, without driving a concurrent chemical reaction. The construction of columns of this type is known in the art.

Starting materials are introduced to column 110 through streams 106 and 108. Stream 106 is a combination of stream 100, which comprises mainly aromatic alcohol, either fresh or recycled, and stream 102, which comprises aromatic alcohol and transesterification catalyst. Optionally, stream 106 can also include alkyl alcohol, alkyl carbonate and side-reaction products recycled from reactive distillation column 138 via stream 144. Stream 100 can be further augmented by a fresh transesterification catalyst stream where fresh transesterification catalyst may be added if required.

Stream 108 is a mixture of stream 104, comprising alkyl alcohol and dialkyl carbonate and recycle stream 132, which comprises dialkyl carbonate, aromatic alcohol and alkyl aryl ether.

Stream 108 is fed into the bottom section of column 110, preferably to the reboiler. The stream may be a liquid or a vapor, depending on the type of reboiler used. For example, if an external reboiler, e.g., a kettle reboiler, is used, stream 108 enters column 110 as a vapor. Stream 106 is fed as a liquid into the middle section of column 110, at a location at or near the top of the reactive distillation section. The feed rate of streams 106 and 108 is such that the molar ratio of dialkyl carbonate to aromatic alcohol is about 0.5 to about 10, preferably about 0.5 to about 5 and most preferably about 1 to about 3, and all subranges therebetween. It is particularly advantageous to provide dialkyl carbonate in excess through stream 108, because dialkyl carbonate serves as both a reactant and a stripping agent and facilitates removal of the alkyl alcohol produced in the transesterification reaction. This removal increases the rate of production of alkyl aryl carbonate in column 110. The transesterification reaction in column 110 is carried out at a temperature of about 100° C. to about 300° C., preferably about 130° C. to about 250° C., and most preferably about 140° C. to about 220° C., and all subranges therebetween. All pressures described herein are absolute pressures. The operating pressure of column 110 is about 5,000 Pascal (Pa) to about 2,000,000 Pa, preferably about 50,000 to about 1,000,000 Pa, and most preferably about 300,000 to about 700,000 Pa, and all subranges therebetween.

In one embodiment reaction products and unreacted starting materials are removed from column 110 as shown in FIG. 1 through streams 112 and 114. Stream 112, which is drawn from the top of the column 10, comprises unreacted dialkyl carbonate, alkyl alcohol and alkyl aryl produced in the transesterification reaction. Stream 112 is split into two streams, 112a and 112b. Stream 112a is passed to rectification column 116 for processing and recovery. Stream 112b is passed to rectification column 146 for further purification of alkyl aryl ether. In one embodiment a splitter may be used to split stream 112.

In another embodiment reaction products and unreacted starting materials are removed from column 110 as shown in FIG. 2 through streams 112, 112c and 114. Stream 112, which is drawn from the top of column 112, comprises unreacted dialkyl carbonate, alkyl alcohol and alkyl aryl ether produced in the transesterification reaction. This stream is passed to rectification column 116 for processing and recovery. Steam 112c is drawn from the side of the column. This stream comprises alkyl aryl ether, dialkyl carbonate and alkyl alcohol. Stream 112c is sent to rectification column 146 for further purification of alkyl aryl ether.

Column 146 is furnished with arranged packings, dumped packings or fixed internals to provide at least about 3 and preferably about 5 to about 50 theoretical distillation steps, and all subranges therebetween. The temperature in the column 146 is about 50 to about 250° C., preferably about 50 to about 200° C., and all subranges therebetween. The pressure in column 146 is at about of 10,000 to about 1,000,000 Pa, preferably about 50,000 to about 200,000 Pa, and all subranges therebetween.

Column 146 separates dialkyl carbonate and alkyl alcohol from alkyl aryl ether and produces substantially pure alkyl aryl ether, which is discharged through stream 142. Recovered dialkyl carbonate and alkyl alcohol is returned to column 116 via stream 140. Stream 140 may be fed directly in vapor form into column 116. In one embodiment as shown in FIG. 1 stream 140 may be merged with stream 112a. In another embodiment as shown in FIG. 2 stream 140 may be merged with 112.

Stream 114, which is drawn from near the bottom of column 110, comprises alkyl aryl carbonate produced in column 110, dialkyl carbonate, aromatic alcohol, alkyl aryl ether and transesterification catalyst. Stream 114 is passed to the second reactive distillation column 124. In one embodiment stream 114 may further comprise diaryl carbonate.

Column 124 has a lower reaction section and an upper rectification section. This column promotes the disproportionation of alkyl aryl carbonate into diaryl carbonate and dialkyl carbonate, while at the same time separating dialkyl carbonate from the reaction mixture.

The reactive and rectification sections of column 124 are each furnished with arranged packings, dumped packings or fixed internals to provide about 1 to about 50, preferably about 5 to about 20 theoretical distillation steps, and all subranges therebetween. The temperature in column 124 is about 50 to about 300° C., preferably about 60 to about 280° C., and most preferably about 100 to about 250° C., and all subranges therebetween.

The pressure in column 124 is maintained at about 5,000 Pa to about 1,000,000 Pa, preferably about 20,000 to about 500,000 Pa, and most preferably about 100,000 to about 300,000 Pa, and all subranges therebetween. It is preferable to maintain the pressure of column 124 below the pressure of column 110. This results in an adiabatic flash of stream 114, hence facilitating separation of dialkyl carbonate from the reaction mixture in column 124. It is also preferable to maintain the pressure of column 124 slightly above the pressure of 116 for integration.

Column 124 is operated in such a way that dialkyl carbonate entering the column through stream 114 is separated from the reaction mixture, hence increasing the rate of the disproportionation reaction taking place in the reactive section. Column 124 can also be utilized as a reboiler for column 116, in which case the two columns are connected by streams 120 and 122 as shown in FIG. 1. In this case, care should be taken to avoid carryover of alkyl aryl carbonate to column 116 in this configuration, since this could result in recycle of alkyl aryl carbonate to column 110 via stream 132. Recycle of alkyl aryl carbonate and alkyl alcohol would drive the composition in column 110 towards the starting materials, hence lowering the net production rate of alkyl aryl carbonate in column 110. Thus, columns 124 and 116 are operated such that stream 120, when present, comprises dialkyl carbonate and alkyl aryl ether in the liquid phase, refluxing back from rectification column 116.

Rectification column 116 produces a top by-product stream 128 comprising a mixture of dialkyl carbonate and alkyl alcohol produced in the process. In one embodiment the top by-product stream 128 comprises an azeotropic mixture of dialkyl carbonate and alkyl alcohol, which can be condensed and reused as a feed stream for a complementary dialkyl carbonate production process without further purification.

Column 116 is furnished with arranged packings, dumped packings or fixed internals to provide at least about 3 and preferably about 5 to about 50 theoretical distillation steps, and all subranges therebetween. The temperature in the column 116 is about 10 to about 200° C., preferably about 50 to about 150° C., and all subranges therebetween. The pressure in column 116 is at about of 10,000 to about 1,000,000 Pa, preferably about 50,000 to about 200,000 Pa, and all subranges therebetween.

In addition to streams 120 and 122, which interchange materials with column 116, materials leave column 124 via stream 134.

Stream 134 comprises diaryl carbonate produced in column 124, dialkyl carbonate, aromatic alcohol, alkyl aryl carbonate, alkyl aryl ether and transesterification catalyst. Stream 134 is fed to reactive distillation column 138, which is furnished with arranged packings, dumped packings or fixed internals. Column 138 provides about 5 to about 80, and more preferably about 20 to about 60 theoretical distillation steps, and all subranges therebetween.

Column 138 is operated to further drive the reaction toward the desired diaryl carbonate product, while separating other materials preferably for recycle. Two streams are removed from column 138. The first is a bottom stream 148, which comprises diaryl carbonate, transesterification catalyst, alkyl aryl carbonate and high boiling by-products. Preferably this product stream is further distilled if additional purification of diaryl carbonate is desired. Diaryl carbonate produced in the disclosed methods can be reacted with bisphenols (e.g., Bisphenol A) for production of polycarbonates.

The second stream 144 is removed from the top of column 138 comprises unreacted aromatic alcohol, dialkyl carbonate and alkyl aryl ether. Stream 144 is preferably recycled to make up part of stream 106.

Column 138 is operated at a temperature of about 100 to about 300° C., preferably about 100 to about 250° C., and most preferably about 140 to about 200° C., and all subranges therebetween. The pressure in the column is at about 1,000 Pa to about 300,000 Pa, preferably about 5,000 Pa to about 100,000 Pa, and most preferably about 10,000 to about 40,000 Pa, and all subranges therebetween.

Within the scope of the process noted above, several variations are possible. For example, the already described interconnection of columns 116 and 124 via streams 120 and 122.

Additionally stream 134 may be augmented by addition of a stream comprising alkyl aryl carbonate via stream 126 to form stream 136. In one embodiment a partial condenser may be connected to the top of the column 110. The partial condenser condenses a portion of the top stream drawn from column 100, which is to be sent back to the column as reflux. The rest of the top stream may be fed to column 116 in vapor form.

It will be appreciated by persons skilled in the art that the positioning of the various streams as described above as being in the top, middle or bottom of the column is necessarily a relative term since the position at which material is to be introduced is dependent on the conditions being maintained in the column. For example, a stream entering the bottom of the column may actually enter a few stages above the sump, and a stream entering the top of the column may enter a few stages below top stage. Nonetheless, these terms are included to define the general orientation of the various columns and streams.

The method and apparatus described above allow the co production of diaryl carbonate and alkyl aryl ether in an efficient manner on an industrial scale.

The method disclosed here is further illustrated in of the following non-limiting examples.

EXAMPLE 1

An Aspen model depicting the process as shown in FIG. 1 was developed and run using Aspen Plus 11.1 simulation software and the results are indicated in Table 1 wherein the reactants used were dimethyl carbonate and phenol in the presence of titaniumtetraphenoxide to produce diphenyl carbonate and anisole. The simulation was run using the feed molar ratio of dimethyl carbonate to phenol of 2.5.

EXAMPLE 2

An Aspen model depicting the process as shown in FIG. 2 was developed and run using Aspen 11.2 simulation software and the results are indicated in Table 1. The feed molar ratio of dimethyl carbonate and phenol was the same as in Example 1.

EXAMPLES 3–17

Figure 3:
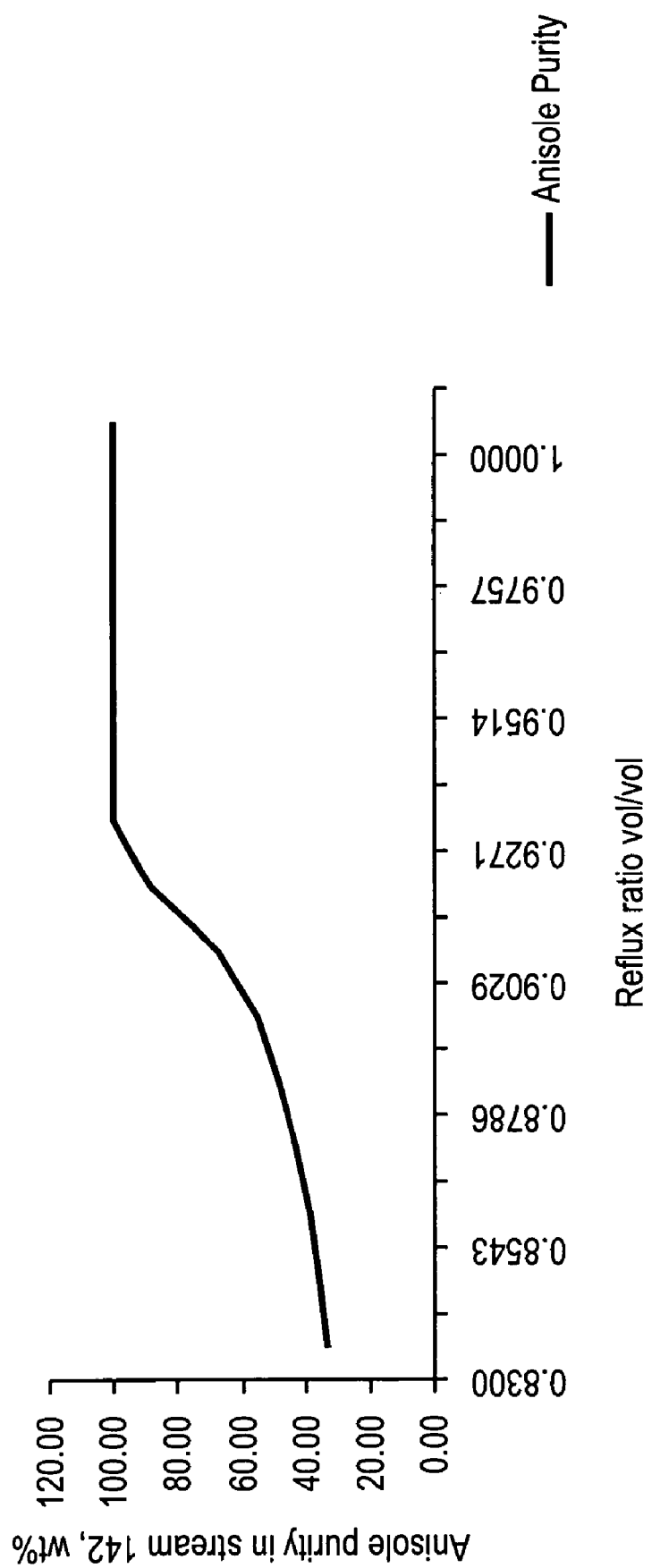
FIG. 3 shows the effect of reflux in column 110 on anisole purity in stream 142.

Keeping the process conditions of Example 1, the Aspen model was run by varying the reflux ratio of column 110 from 0.83 to 1.0. The results showing the anisole purity (in weight %) in stream 142 by changing the reflux ratio in column 110 is shown in Table 2. FIG. 3 also shows the graphical representation of the data in table 2. It shows that as the reflux ratio is increased the purity of anisole in stream 142 increases.

EXAMPLE 18

A comparative example was run by developing an Aspen model flow sheet based on a configuration wherein the anisole rich stream is drawn from the side of the second reactive distillation column. All other process conditions were same as in Example 1 and 2. The results show that in both the process options of the disclosed methods as depicted in FIGS. 1 and 2, the anisole purity in stream 142 is more than what is achieved by drawing the anisole rich stream from side of second reactive distillation column under similar process conditions. Furthermore a comparison of the steam consumption predicted by Aspen simulation model of all the processes is also shown in Table 1. The comparative Example 18 where the anisole rich stream is drawn from the side of the second reactive distillation column, shows maximum steam consumption of 5.40 ton per ton of diphenyl carbonate produced whereas the disclosed methods as shown in two embodiments in FIG. 1 and FIG. 2 show steam consumption of 5.20 and 5.10 tons per ton of diphenyl carbonate produced respectively.

TABLE 1

|  | Comparative Example, side draw from second reactive distillation column Example 18 | | | | Column 110 Distillate split, simulation of process depicted in FIG. 1 Example 1 | | | |
| --- | --- | --- | --- | --- | --- | --- | --- | --- |
| Stream Number | 6 | 5 | 12 | 13 | 114 | 112 | 112b | 142 |
| Temperature Deg C | 214.00 | 136.20 | 129.20 | 185.90 | 214.00 | 136.20 | 136.20 | 183.60 |
| Pressure Pascal | 593000 | 539100 | 251300 | 214000 | 593000 | 539100 | 251300 | 214000 |
| Composition (weight %) | | | | | | | | |
| carbondioxide | 0.00 | 0.02 | 0.00 | 0.00 | 0.00 | 0.02 | 0.02 | 0.00 |
| methanol | 0.10 | 5.17 | 0.05 | 0.00 | 0.10 | 5.38 | 5.38 | 0.00 |
| phenol | 36.80 | 0.44 | 1.18 | 10.16 | 38.10 | 0.00 | 0.00 | 0.02 |
| dimethyl carbonate | 28.14 | 88.50 | 52.99 | 0.00 | 28.57 | 91.38 | 91.38 | 0.10 |
| phenyl m thyl carbonate | 21.19 | 0.00 | 0.01 | 0.05 | 21.69 | 0.00 | 0.00 | 0.00 |
| diphenyl carbonate | 2.03 | 0.00 | 0.00 | 0.00 | 2.10 | 0.00 | 0.00 | 0.00 |
| anisole | 9.78 | 5.87 | 45.77 | 89.79 | 7.42 | 3.22 | 3.22 | 99.88 |
| others including catalyst | 1.95 | 0.00 | 0.00 | 0.00 | 2.02 | 0.00 | 0.00 | 0.00 |
| total | 100.00 | 100.00 | 100.00 | 100.00 | 99.99 | 100.00 | 100.00 | 100.00 |
| ton of steam consumption per ton of DPC produced | | 5.4024 | | | | 5.1981 | | |

|  | Column 110 side draw, simulation of process depicted in FIG. 2 Example 2 | | | |
| --- | --- | --- | --- | --- |
| Stream Number | 114 | 112 | 112c | 142 |
| Temperature | 214.00 | 136.20 | 153.20 | 183.60 |
| Pressure Pascal | 593000 | 539100 | 251300 | 214000 |

TABLE 1-continued

| Composition (weight %) | | | | |
|---|---|---|---|---|
| carbondioxide | 0.00 | 0.02 | 0.00 | 0.00 |
| methanol | 0.10 | 5.42 | 0.96 | 0.00 |
| phenol | 39.45 | 0.00 | 0.01 | 0.05 |
| dimethyl carbonate | 29.05 | 92.74 | 85.16 | 0.10 |
| phenyl m thyl carbonate | 22.53 | 0.00 | 0.00 | 0.00 |
| diphenyl | 2.23 | 0.00 | 0.00 | 0.00 |
| anisole | 4.45 | 1.82 | 13.88 | 99.85 |
| others including catalyst | 2.18 | 0.00 | 0.00 | 0.00 |
| total | 99.99 | 100.00 | 100.00 | 100.00 |
| ton of steam consumption per ton of DPC produced | | 5.0969 | | |

TABLE 2

| Example No. | Reflux ratio in 110 | Anisole Purity in stream 142 (weight %) |
|---|---|---|
| 3 | 0.8300 | 33.56 |
| 4 | 0.8421 | 36.06 |
| 5 | 0.8543 | 39.11 |
| 6 | 0.8664 | 42.99 |
| 7 | 0.8786 | 48.14 |
| 8 | 0.8907 | 55.46 |
| 9 | 0.9029 | 67.09 |
| 10 | 0.9150 | 89.47 |
| 11 | 0.9271 | 100.00 |
| 12 | 0.9393 | 100.00 |
| 13 | 0.9514 | 100.00 |
| 14 | 0.9636 | 100.00 |
| 15 | 0.9757 | 100.00 |
| 16 | 0.9879 | 100.00 |
| 17 | 1.0000 | 100.00 |

All patents cited herein are incorporated by reference.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for continuously producing an alkyl aryl ether comprising:
    reacting a dialkyl carbonate and an aromatic alcohol in the presence of a transesterification catalyst in a first reactive distillation column;
    recovering from said first reactive distillation column a stream comprising said dialkyl carbonate, said alkyl alcohol and said alkyl aryl ether;
    separating said alkyl aryl ether in said stream from said dialkyl carbonate and alkyl alcohol in a rectification column; and
    recovering from said rectification column a product stream comprising substantially pure said alkyl aryl ether;
    wherein said product stream comprises at least about 95% said alkyl aryl ether by weight.

2. The method according to claim 1 wherein said stream is drawn from the top of said first reactive distillation column.

3. The method according to claim 1 wherein said stream is drawn from the side of said first reactive distillation column.

4. The method according to claim 1 wherein said first reactive distillation column is maintained at a temperature of about 100 to about 300° C.

5. The method according to claim 4 wherein said first reactive distillation column is maintained at a temperature of about 140 to about 220° C.

6. The method according to claim 1 wherein said first reactive distillation column is maintained at a pressure of about 5,000 Pascal to about 2,000,000 Pascal.

7. The method according to claim 6 wherein said first reactive distillation column is maintained at a pressure of about 300,000 to about 700,000 Pascal.

8. The method according to claim 1 wherein said rectification column is maintained at a temperature of about 50 to about 150° C.

9. The method according to claim 1 wherein said rectification column is maintained at a pressure of about 50,000 Pascal to about 200,000 Pascal.

10. The method according to claim 1 wherein said product stream comprises at least about 99% of said alkyl aryl ether by weight.

11. A method for continuously producing a diaryl carbonate and an alkyl aryl ether comprising:
    reacting a dialkyl carbonate and an aromatic alcohol in the presence of a transesterification catalyst in a first reactive distillation column;
    recovering from said first reactive distillation column a first top steam comprising said dialkyl carbonate, said alkyl alcohol and said alkyl aryl ether;
    splitting said first top stream into a first split steam and a second split stream;
    recovering from said first reactive distillation column a first bottom stream comprising said alkyl aryl carbonate, dialkyl carbonate, aromatic alcohol, alkyl aryl either and transesterification catalyst;
    introducing said first bottom stream into a second reactive distillation column;
    recovering from said second reactive distillation column a second bottom stream comprising said diaryl carbonate, alkyl aryl carbonate, dialkyl carbonate, aromatic alcohol and transesterification catalyst;
    introducing said second split stream into a second rectification column, separating said dialkyl carbonate and said alkyl alcohol from said alkyl aryl ether, and recycling said dialkyl carbonate and said alkyl alcohol to a first rectification column;

introducing said first split stream into said first rectification column;

recovering from said first rectification column a second top stream comprising said dialkyl carbonate and alkyl alcohol, and a third bottom stream comprising said dialkyl carbonate, and recycling part of said third bottom stream to said first reactive distillation column;

recovering a first product stream from bottom of said second rectification column comprising substantially pure said alkyl aryl ether;

introducing said second bottom stream into a third reactive distillation column;

recovering a second product stream comprising diaryl carbonate produced from the bottom of said third reactive distillation column and a third top stream comprising aromatic alcohol, dialkyl carbonate and alkyl aryl ether; and recycling said third top stream to said first reactive distillation column.

12. The method according to claim 11 wherein said second reactive distillation column is maintained at a temperature of about 50 to about 300° C.

13. The method according to claim 12 wherein said second reactive distillation column is maintained at a temperature of about 100 to about 250° C.

14. The method according to claim 11 wherein said second reactive distillation column is maintained at a pressure of about 5,000 Pascal to about 1,000,000 Pascal.

15. The method according to claim 14 wherein said second reactive distillation column is maintained at a pressure of about 100,000 to about 300,000 Pascal.

16. The method according to claim 11 wherein said third reactive distillation column is maintained at a temperature of about 100 to about 300° C.

17. The method according to claim 16 wherein said third reactive distillation column is maintained at a temperature of about 140 to about 200° C.

18. The method according to claim 11 wherein said third reactive distillation column is maintained at a pressure of about 1,000 Pascal to about 300,000 Pascal.

19. The method according to claim 18 wherein said third reactive distillation column is maintained at a pressure of about 10,000 to about 40,000 Pascal.

20. The method according to claim 11 wherein said second reactive distillation column is maintained at a pressure lower than the pressure in said first reactive distillation column.

21. The method according to claim 11 wherein the first top stream is introduced to a partial condenser.

22. A method for continuously producing an alkyl aryl ether comprising:

reacting a dialkyl carbonate and an aromatic alcohol in the presence of a transesterification catalyst in a first reactive distillation column;

recovering from said first reactive distillation column a side stream comprising said dialkyl carbonate, said alkyl alcohol and said alkyl aryl ether;

separating said alkyl aryl ether in said side stream from said dialkyl carbonate and alkyl alcohol in a rectification column; and recovering from bottom of said rectification column a product stream comprising substantially pure said alkyl aryl ether.

23. An apparatus for continuous production of a substantially pure alkyl aryl ether comprising first and second reactive distillation columns, and first and second rectification columns and a plurality of streams for transporting reactant and product streams, wherein:

said first reactive distillation column is connected to input streams, and to first, second and third transfer streams, said first transfer stream running from the top of said first reactive distillation column to said first rectification column; said second transfer stream running from the side of said first reactive distillation column to said second rectification column and said third transfer stream running from the bottom of said first reactive distillation column to said second reactive distillation column; and said second rectification column is connected to a product stream running from the bottom for recovering alkyl aryl ether and a recycle stream running from the top to said first rectification column.

24. An apparatus for continuous production of diaryl carbonate and alkyl aryl ether comprising first, second and third reactive distillation columns, first and second rectification column, a splitter and a plurality of streams for transporting reactant and product streams, wherein:

said first reactive distillation column is connected to input streams for the introduction of reactants, and to first and second transfer streams, said first transfer stream running from the top of said first reactive distillation column to said splitter; said second transfer stream running from the bottom of said first reactive distillation column to said second reactive distillation column;

said splitter is connected to first and second split streams, said first split stream running from said splitter to said first rectification column and said second split stream running from said splitter to said second rectification column;

second reactive distillation column is connected to third and fourth transfer streams, said third transfer stream running from the top of said second reactive distillation column to the bottom of said first rectification column, and said fourth transfer stream running from the bottom of said second reactive distillation column to said third reactive distillation column;

said third reactive distillation column is connected to a second product stream for providing diaryl carbonate product from the bottom of said third reactive distillation column and a first recycle steam running from the top of said third reactive distillation column to said first reactive distillation column;

said first rectification column is connected to a third product stream for providing dialkyl carbonate/alkyl alcohol mixture from the top of said first rectification column, and a second recycle stream running from the bottom of said first rectification column to the bottom of said first reactive distillation column; and said second rectification column is connected to a first product stream for recovering said alkyl aryl ether from the bottom of said second rectification column and a third recycle stream running from the top of said second rectification column to the middle of said first rectification column.

25. A method of making polycarbonate and substantially pure alkyl aryl ether, said method comprises reacting a bisphenol with a diaryl carbonate wherein said diaryl carbonate and said alkyl aryl ether is prepared by:
   reacting a dialkyl carbonate and an aromatic alcohol in the presence of a transesterification catalyst in a first reactive distillation column;
   recovering from said first reactive distillation column a stream comprising said dialkyl carbonate, said alkyl alcohol and said alkyl aryl ether;
   separating said alkyl aryl ether in said stream from said dialkyl carbonate and alkyl alcohol in a rectification column; and
   recovering from said rectification column a product stream comprising substantially pure said alkyl aryl ether.

* * * * *